United States Patent [19]

Abe et al.

[11] Patent Number: 5,668,883

[45] Date of Patent: Sep. 16, 1997

[54] HEADPHONE APPARATUS INCLUDING AN EQUALIZER SYSTEM HAVING AN OPEN LOOP CHARACTERISTIC WITH A RISING SLOPE OUTSIDE THE CANCELLATION BAND

[75] Inventors: Kensaku Abe, Saitama; Takahiro Muraguchi, Tokyo, both of Japan

[73] Assignee: Sony Corporation, Tokyo, Japan

[21] Appl. No.: 518,723

[22] Filed: Aug. 24, 1995

[30] Foreign Application Priority Data

Sep. 5, 1994 [JP] Japan .................................. 6-234522

[51] Int. Cl.$^6$ .................................................. A61F 11/06
[52] U.S. Cl. .................................................. 381/72; 381/74
[58] Field of Search .................................... 381/71, 72, 74,
381/25, 68.2, 68.4, 68.6, 69, 68, 154, 158,
169, 183, 187; 181/148, 130, 132, 135,
137, 129

[56] References Cited

U.S. PATENT DOCUMENTS

| | | | |
|---|---|---|---|
| 4,455,675 | 6/1984 | Bose et al. | 381/71 |
| 5,022,486 | 6/1991 | Miura et al. | 381/154 |
| 5,228,089 | 7/1993 | Inanaga et al. | 381/69 |
| 5,276,740 | 1/1994 | Inanaga et al. | 381/72 |

*Primary Examiner*—Curtis Kuntz
*Assistant Examiner*—Ping W. Lee
*Attorney, Agent, or Firm*—Jay H. Maioli

[57] ABSTRACT

A headphone includes an acoustic pipe, a loudspeaker unit, a microphone unit and a feedback circuit. The acoustic pipe has an inner diameter substantially equal to that of an external auditory canal. The acoustic pipe has a mounting portion provided at an end thereof for being mounted on the outer ear and has an acoustically non-reflective end at the other end thereof. The loudspeaker unit is provided on one side of the acoustic pipe with a sound emitting face thereof opposed to the inside of the acoustic pipe. The microphone unit is provided on the one side of the acoustic pipe with a sound collecting face thereof opposed to the inside of the acoustic pipe. The feedback circuit feeds back an output signal of the microphone unit to an input side of the loudspeaker unit. The feedback circuit includes an equalizing section. The output signal of the microphone unit is supplied to the loudspeaker unit by way of the equalizing section. The equalizing section has an open loop characteristic wherein an attenuation characteristic in a frequency band other than a frequency band in which noise can be canceled rises higher than an attenuation characteristic in the frequency band in which noise can be canceled.

4 Claims, 5 Drawing Sheets

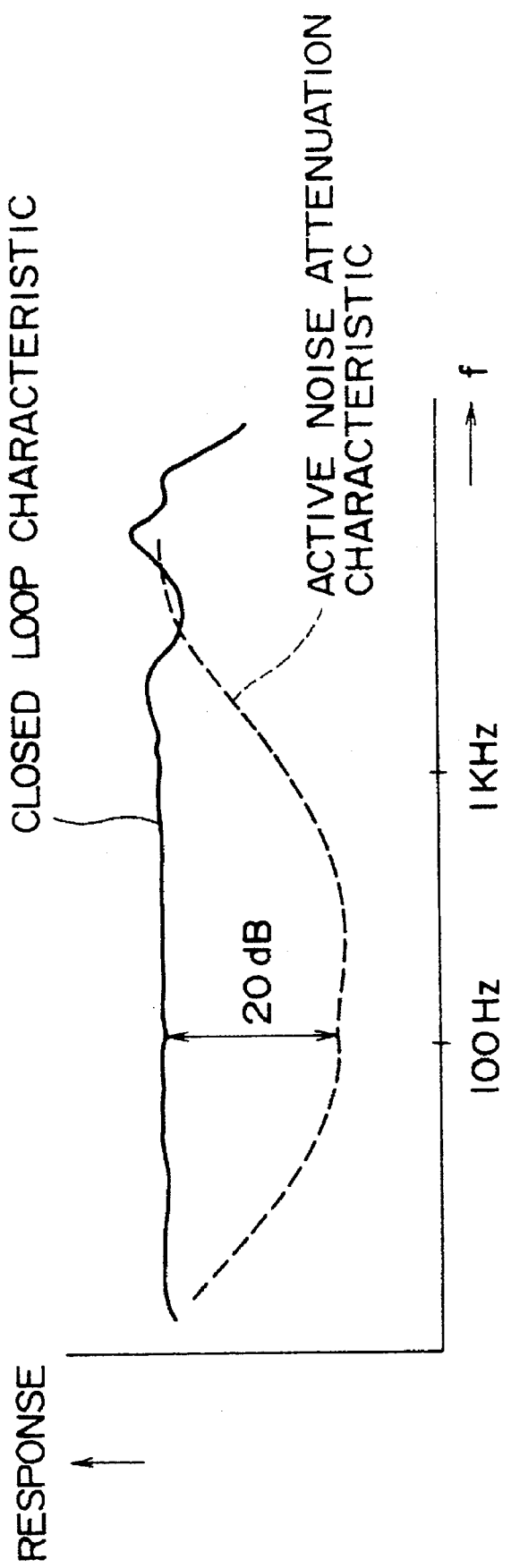

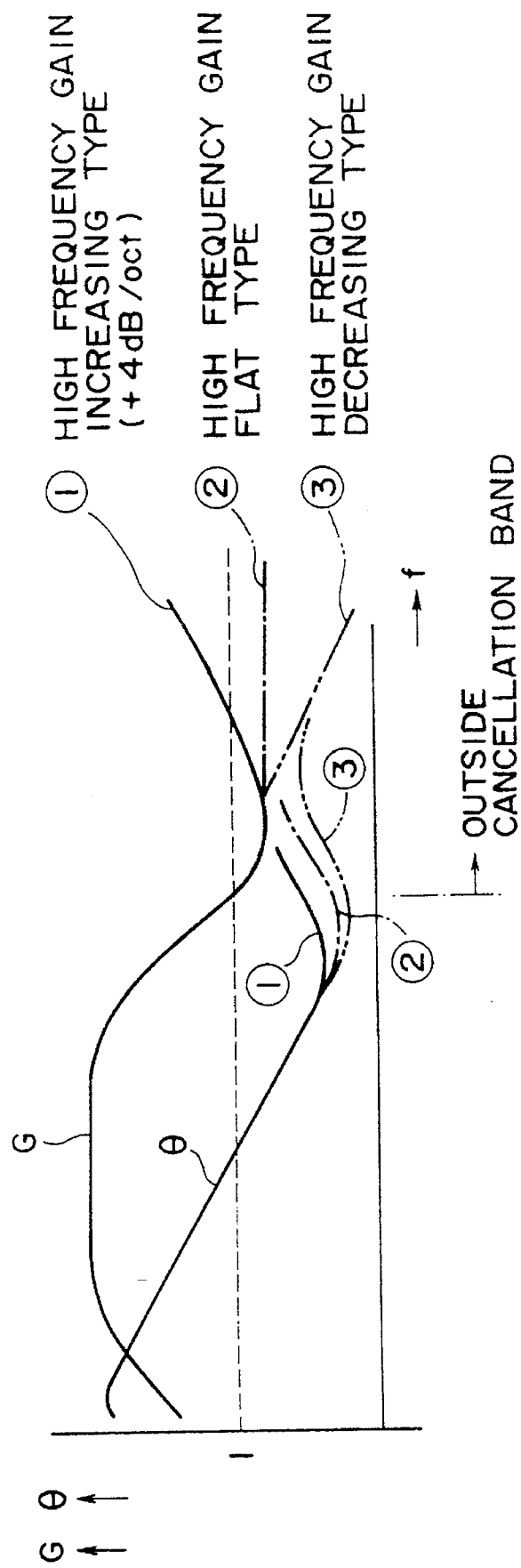

OPEN LOOP CHARACTERISTIC

① HIGH FREQUENCY GAIN INCREASING TYPE

② HIGH FREQUENCY GAIN FLAT TYPE

③ HIGH FREQUENCY GAIN DECREASING TYPE

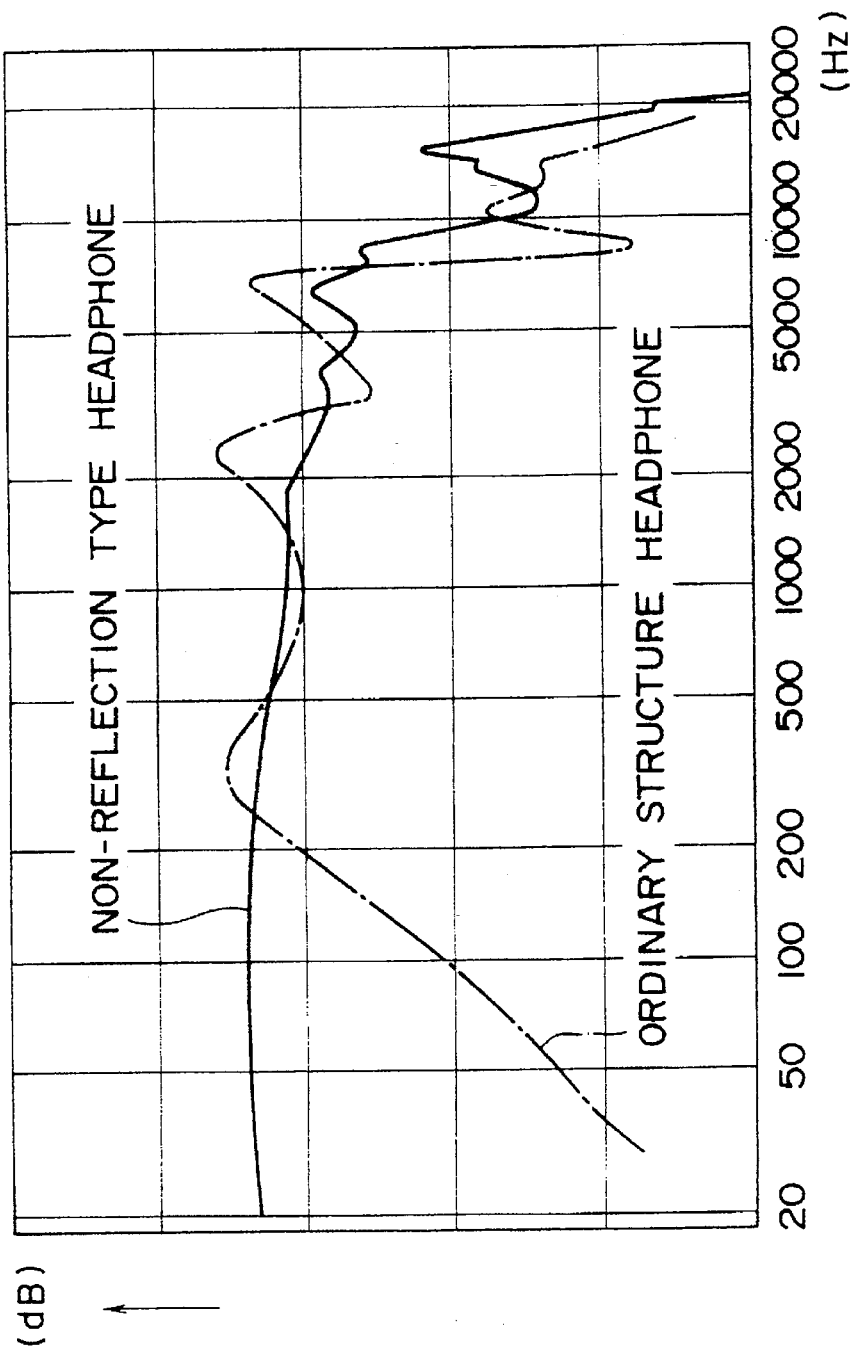

HEADPHONE APPARATUS INCLUDING AN EQUALIZER SYSTEM HAVING AN OPEN LOOP CHARACTERISTIC WITH A RISING SLOPE OUTSIDE THE CANCELLATION BAND

BACKGROUND OF THE INVENTION

1. Field of the Invention

This invention relates to a headphone apparatus, and more particularly to a headphone apparatus having a function of canceling noise from the outside.

2. Description of the Related Art

A headphone of the type wherein a noise component which comes into a cavity between a headphone unit of a headphone and an ear from the outside is detected by means of a microphone and an output signal of the microphone is fed back to a loudspeaker of the headphone unit to reduce noise from the outside is already known. The operation principle of such noise cancellation operation of the headphone is known as feedback theory based on the Bode's theorem. In particular, the attenuation amount of noise and the bandwidth of frequencies in which noise can be canceled are characterized by an open loop characteristic.

Generally, in order to stabilize a closed loop characteristic to prevent oscillations or the like, it is required that the attenuation characteristic outside a frequency band in which noise can be canceled (hereinafter referred to merely as the noise canceling band) be −6 dB/oct to −12 db/oct.

In the meantime, also a technique of making the attenuation characteristic outside a canceling band substantially flat has been proposed as disclosed, for example, in U.S. Pat. No. 4,455,675.

However, an increase of the active band, that is, the noise canceling band of a wide band reproduction headphone which can reproduce sound in a frequency band of substantially 20 Hz to 10 KHz cannot be realized if the gain characteristic of the open loop characteristic of a feedback loop outside the noise canceling band is set to a dropping characteristic or to a substantially flat characteristic as described above. This is because, when the noise canceling band is widened, oscillations occur in a high frequency portion of the noise canceling band. One kind of wide band reproduction headphones is a headphone of the non-reflective type wherein an acoustic pipe having an ear mounting portion at an end portion thereof and a non-reflective end for sound at the other end thereof and having an inner diameter substantially equal to an external auditory canal is provided and a headphone unit is mounted on the acoustic pipe such that a sound emitting face thereof is opposed to the inside of the pipe. A non-reflective headphone of the type just described is disclosed in U.S. Pat. No. 5,022,486.

SUMMARY OF THE INVENTION

It is therefore an object of the present invention to provide a headphone which resolves the above-mentioned problem.

According to the present invention, there is provided a headphone comprising an acoustic pipe, a loudspeaker unit, a microphone unit and a feedback circuit. The acoustic pipe has an inner diameter substantially equal to that of an external auditory canal. The acoustic pipe has a mounting portion provided at an end thereof for being mounted on the outer ear and has an acoustically non-reflective end at the other end thereof. The loudspeaker unit is provided on one side of the acoustic pipe with a sound emitting face thereof opposed to the inside of the acoustic pipe. The microphone unit is provided on the one side of the acoustic pipe with a sound collecting face thereof opposed to the inside of the acoustic pipe. The feedback circuit feeds back an output signal of the microphone unit to an input side of the loudspeaker unit. The feedback circuit includes an equalizing section. The output signal of the microphone unit is supplied to the loudspeaker unit by way of the equalizing section. The equalizing section has an open loop characteristic wherein an attenuation characteristic in a frequency band other than a frequency band in which noise can be canceled rises higher than an attenuation characteristic in the frequency band in which noise can be canceled.

With the headphone of the present invention, since the open loop characteristic of the equalizing section by way of which the output signal of the microphone unit provided on the acoustic pipe having an inner diameter substantially equal to that of the external auditory canal is fed back to the loudspeaker unit also provided on the acoustic pipe is set to the characteristic wherein the attenuation characteristic outside the frequency band in which noise can be canceled rises higher than the attenuation characteristic in the frequency characteristic in which noise can be canceled, the noise attenuation amount can be increased and the frequency band in which noise can be canceled can be widened.

BRIEF DESCRIPTION OF THE DRAWINGS

FIG. 2 is a diagram illustrating an active noise attenuation characteristic and a closed loop characteristic of the headphone apparatus shown in FIG. 1;

FIG. 3 is a diagram illustrating an open loop characteristic of an equalizer and an amplifier of the headphone apparatus of FIG. 1 in comparison with open loop characteristics of an equalizer and an amplifier of comparative examples;

FIGS. 4a through 4c are diagrams illustrating the open loop characteristic of the headphone apparatus of FIG. 1 and the open loop characteristics of the comparative examples shown in FIG. 3, and wherein FIG. 4a illustrates the open loop characteristic of the headphone apparatus of FIG. 1, FIG. 4b illustrates the open loop characteristic of one of the comparative examples shown in FIG. 3, and FIG. 4c illustrates the open loop characteristic of the other comparative example shown in FIG. 3; and FIG. 5 is a diagram illustrating a frequency characteristic of a headphone of an open air type as a comparative example and a frequency characteristic of a non-reflective headphone as the headphone apparatus shown in FIG. 1.

DETAILED DESCRIPTION OF THE PREFERRED EMBODIMENT

In the following, a headphone apparatus according to a preferred embodiment of the present invention will be described in detail with reference to the drawings.

Figure 1:
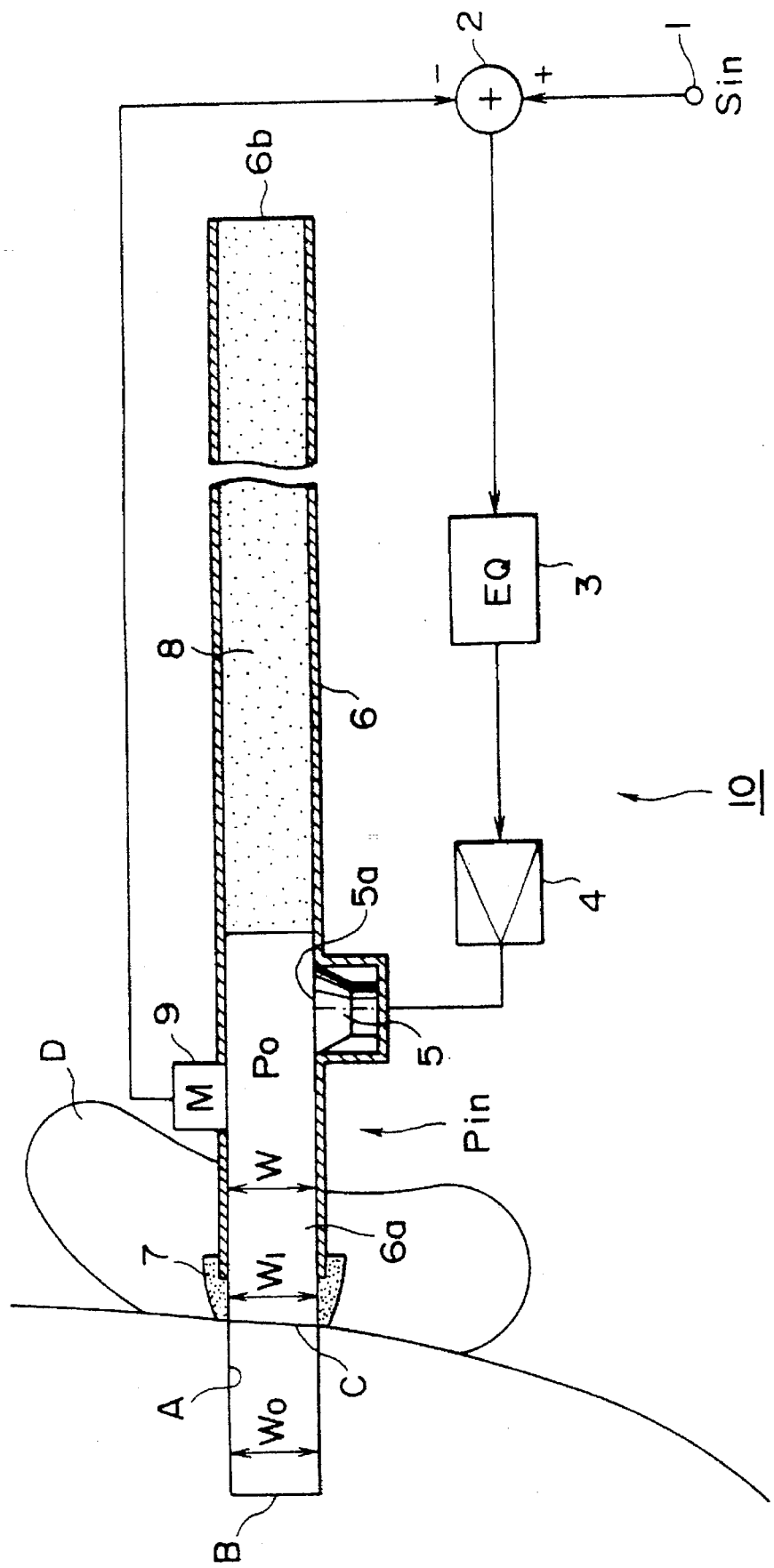
FIG. 1 is a sectional view showing a construction of a headphone apparatus according to a preferred embodiment of the present invention.

FIG. 1 shows a structure of a headphone apparatus 10 of the present invention. The headphone apparatus 10 can be used as an electro-acoustic transducer for a headphone apparatus connected to an acoustic reproduction apparatus or a hearing aid. It is to be noted that, where the headphone apparatus 10 of the structure shown in FIG. 1 is adopted for an acoustic apparatus which outputs L (left) and R (right) stereo sounds, the headphone apparatus 10 is provided with two units corresponding to the left and right ears.

A reproduction signal from an audio apparatus or an amplified signal of an output signal of a microphone of a hearing aid is inputted as an input audio signal Sin to an audio input terminal 1 of the headphone apparatus 10.

The audio signal inputted from the audio input terminal 1 is supplied to a loudspeaker unit 5 by way of a subtractor 2, an equalizer 3 and an amplifier 4. The audio signal is electro-acoustically converted by the loudspeaker unit 5 and comes to the ear-drum by way of an acoustic pipe which will be hereinafter described. Meanwhile, noise originating from the outside and coming to the inside of the acoustic pipe is picked up by a microphone unit 9. An output signal of the microphone unit 9 is supplied to the subtractor 2.

An acoustic pipe 6 is formed as an elongated pipe or tube and is open at an end portion 6b thereof. An acoustic material 8 is filled in the inside of the acoustic pipe 6. The loudspeaker unit 5 is mounted on a side wall of the acoustic pipe 6, thereby constructing a headphone of the non-reflective type.

The loudspeaker unit 5 is mounted on the acoustic pipe 6 such that a sound emitting face 5a thereof is opposed to the inside of the acoustic pipe 6 as shown in FIG. 1.

The acoustic pipe 6 is formed as an elongated pipe having an inner diameter W substantially equal to the inner diameter $W_0$ of the external auditory canal A, and an ear piece 7 is mounted at an end portion 6a of the acoustic pipe 6. The other end portion 6b of the acoustic pipe 6 is open as a non-reflective termination for sound, and the acoustic material 8 is filled between a location of the acoustic pipe 6 in the proximity of the loudspeaker unit 5 and the end portion 6b of the acoustic pipe 6.

The ear piece 7 mounted at the end portion 6a of the acoustic pipe 6 is formed from a synthetic resin or a like material having flexibility such that an end portion thereof can be mounted in an entrance portion C of the external auditory canal A of the ear D. The ear piece 7 has an inner diameter $W_1$ substantially equal to the inner diameter W of the acoustic pipe 6 and the inner diameter $W_0$ of the external auditory canal.

The sound emitting face 5a of the loudspeaker unit 5 is provided such that it is opposed substantially flush with the inner circumferential face of the acoustic pipe 6 so that the loudspeaker unit 5 can be mounted without disturbing the acoustic impedance characteristic of the acoustic pipe 6.

In a condition wherein the acoustic pipe 6 is mounted with the end portion of the ear piece 7 mounted in the entrance portion C of the external auditory canal A of the ear D, the external auditory canal of the ear D and the acoustic pipe 6 from the ear-drum B to the end portion 6b of the acoustic pipe 6 formed as a non-reflective termination continue with a substantially fixed inner diameter, and the acoustic pipe 6 thus provides a sound passage having a fixed acoustic impedance.

In the headphone apparatus having the construction described above, sound output from the loudspeaker unit 5 propagates as plane waves to the opposite sides (to the end portion 6a side and the end portion 6b side) in the acoustic pipe 6.

Of the acoustic waves, those acoustic waves which come to and are reflected from the ear-drum B go back to the acoustic pipe 6 side. However, since impedance matching is established with the acoustic pipe 6, the acoustic waves propagate from the end portion 6a side toward the end portion 6b side in the acoustic pipe 6 without being reflected from any other location.

The acoustic waves reflected from the ear-drum B are attenuated gradually before they reach the end portion 6b, and little sound arrives at the end portion 6b.

With the headphone apparatus 10 constructed in such a manner as described above, reflected sound in the headphone itself is not generated by the acoustic pipe 6 or the loudspeaker unit 5.

A frequency characteristic of the headphone apparatus 10 is indicated by a solid line in FIG. 5. It is to be noted that an alternate long and short dash line in FIG. 5 represents a frequency characteristic of an ordinary headphone of the open air type, Model MDR-25 by Sony Corporation.

While a flat characteristic down to a sufficiently low frequency region is obtained with the headphone apparatus 10 as seen in FIG. 5, this indicates that there is no leak from a coupling portion of the headphone apparatus 10 to the external auditory canal A, and that there is no leak signifies that, where the headphone apparatus 10 is used with a hearing aid, a great howling margin can be provided. It is to be noted that, in this instance, the acoustic gain obtained is higher than 40 dB and it is proved that a great howling margin is provided.

Referring back to FIG. 1, the microphone unit 9 is mounted on the acoustic pipe 6 such that it is opposed to the inner face of the acoustic pipe 6. Naturally, also the microphone unit 9 is mounted such that it does not disturb the acoustic impedance characteristic of the acoustic pipe 6 similar to the loudspeaker unit 5.

An output signal of the microphone unit 9 is supplied to the subtractor 2, by which it is subtracted from the input signal Sin. From the subtractor 2, a signal obtained by subtraction of the output signal of the microphone unit 9 from the input signal Sin is outputted.

In short, the output of the microphone unit 9 is fed back to the signal input system to the loudspeaker unit 5, thereby constructing a noise cancellation circuit of the feedback type.

Noise Pin admitted into the inside of the acoustic pipe 6 of the headphone apparatus 10 from the outside is examined here. A sound pressure Po acting upon the ear-drum B is given, from the character of feedback, by $$Po = (1/\text{loop gain}) \times Pin$$

Consequently, the noise Pin arrives at the ear-drum B after it is attenuated by an amount corresponding to the loop gain.

In FIG. 2, an active noise attenuation amount is indicated by a broken line, and a frequency characteristic of a closed loop response is indicated by a solid line. The difference between the active noise attenuation amount and the frequency characteristic of the closed loop response in FIG. 2 is a canceling amount by which noise admitted in from the outside can be canceled. In the example shown in FIG. 2, the maximum canceling amount is approximately 20 dB.

The loop response to the input signal Si is given by $$Po = \{(E \cdot A \cdot H)/(1 + E \cdot A \cdot H \cdot M)\} \times Sin$$
$$\approx (1/M) \times Sin$$

where E is the transfer characteristic of the equalizer 3, A is the transfer characteristic of the amplifier 4, H is the transfer characteristic of the loudspeaker unit 5, and M is the transfer characteristic of the microphone unit 9.

From the expression above, the loop response to the input signal Sin relies upon the transfer characteristic of the microphone unit 9 for feedback.

Where the microphone unit 9 includes an electret capacitor microphone, since it exhibits a flat frequency characteristic over a wide band, the closed loop characteristic of the noise cancellation circuit is such a flat characteristic as indicated by the solid line in FIG. 2.

Here in the present embodiment, the headphone apparatus is constructed so as to realize expansion of the frequency bandwidth in which noise can be canceled as well as increase the attenuation amount of noise to be cancelled, that is, increase of the active attenuation amount by means of the noise cancellation circuit of the feedback type having the construction described above.

Therefore, the characteristics provided by the equalizer 3 and the amplifier 4 are set as indicated by lines ① in FIG. 3. This will be described below.

FIG. 3 illustrates gains G and phases θ as transfer characteristics E and A of the equalizer 3 and the amplifier 4. In the present embodiment, as seen from the lines ① in FIG. 3, the gains G and the phases θ are characterized in characteristics outside the canceling band particularly on the high frequency side. It is to be noted that the terminology "outside the canceling band" signifies a frequency band in which the gain G is lower than 1. To which frequency band the canceling band, that is, the frequency band in which noise can be canceled, is to be set can be varied by varying the transfer characteristic of the equalizer 3 and/or the transfer characteristic of the amplifier 4.

The characteristics indicated by lines ③ in FIG. 3 are characteristics of a conventional system, and with the characteristics, the gain characteristic outside the canceling band exhibits a drop, for example, by minus several dB/oct (hereinafter referred to as high frequency gain dropping type).

With the characteristics indicated by lines ② in FIG. 3, the gain characteristic outside the canceling band is flat almost with 0 dB/oct (hereinafter referred to as high frequency gain flat type).

Finally, the characteristics indicated by lines ① in FIG. 3 are obtained in the present embodiment, and with the characteristics, the gain characteristic outside the canceling band exhibits a rise, for example, by plus several dB/oct (hereinafter referred to as high frequency gain rising type). In the present embodiment, the gain characteristic is, for example, +4 dB/oct.

Also the phase characteristics of the characteristics ①, ② and ③ in FIG. 3 are different from one another as seen in FIG. 3.

Where a headphone of the non-reflective type is constructed as a headphone apparatus as in the present embodiment, it has been proved by an experiment that, when the transfer characteristics E and A of the equalizer 3 and the amplifier 4 are set to characteristics of the high frequency gain rising type indicated by the lines ① in FIG. 3, the attenuation amount by which noise can be canceled, that is, the active noise attenuation amount, is maximum and also the stability against oscillations in a high frequency band in the frequency band in which noise can be canceled even if the frequency band in which noise can be canceled is widened is in the maximum.

Figure 4A:
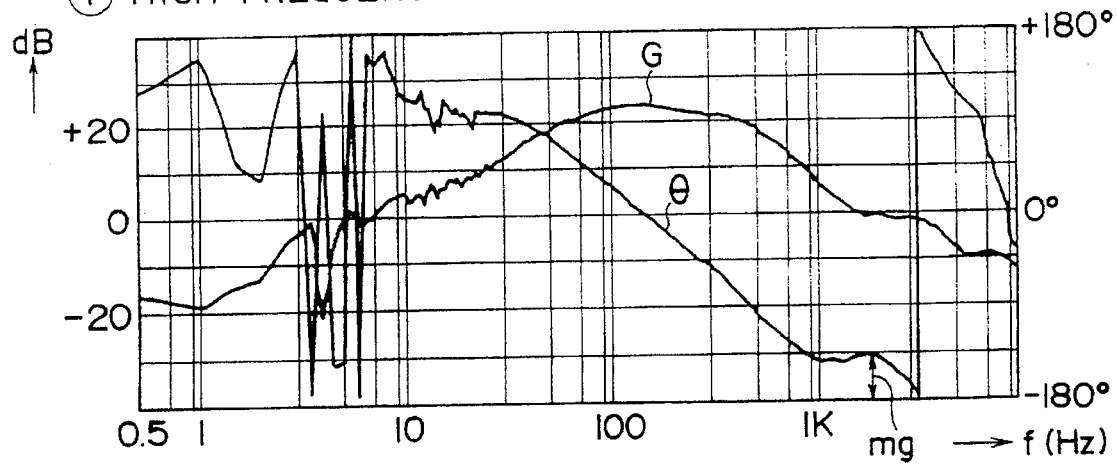
Figure 4B:
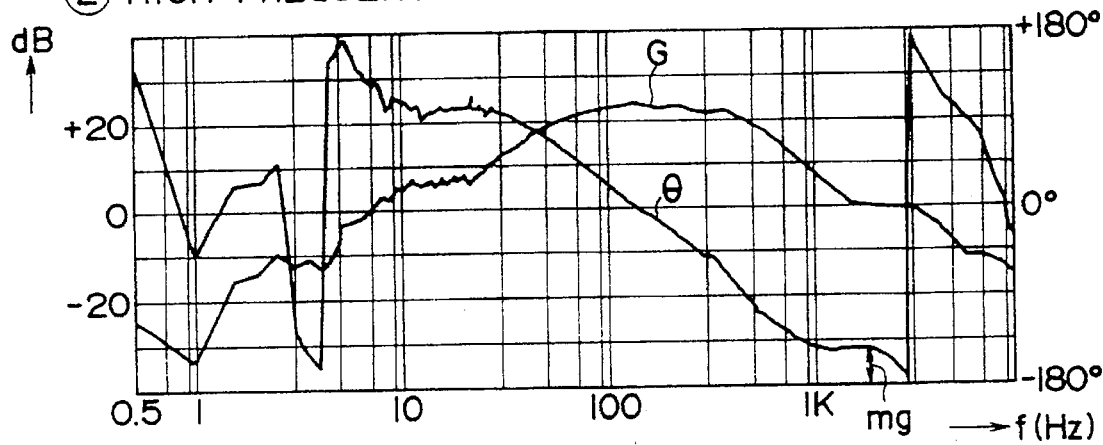
Figure 4C:
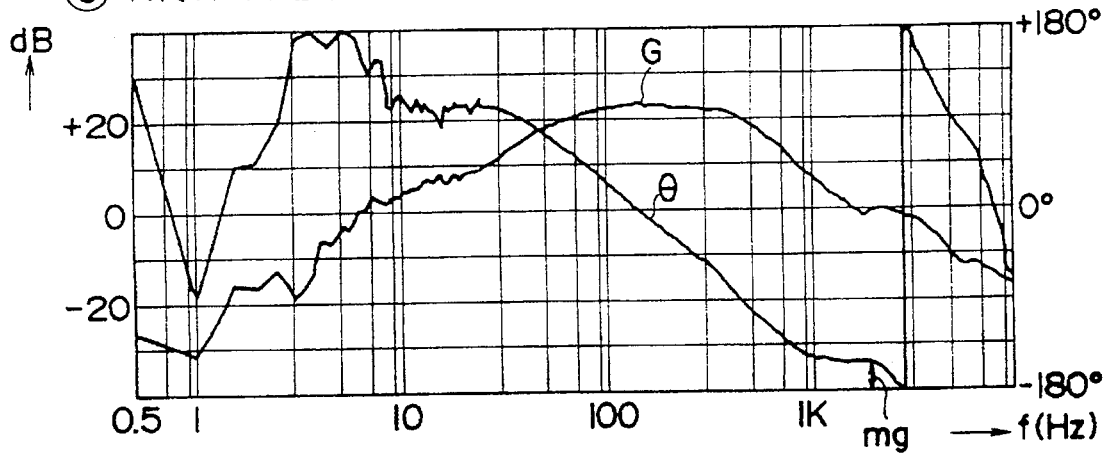

FIGS. 4a, 4b and 4c illustrate open loop characteristics where the characteristics indicated by the lines ①, ② and ③ in FIG. 3 are adopted, respectively. The open loop characteristics are overall characteristics by the transfer characteristic E of the equalizer 3, the transfer characteristic A of the amplifier 4, the transfer characteristic of the loudspeaker unit 5 and the transfer characteristic of the microphone unit 9.

In these characteristics, if the phase θ is different over 180 degrees in the condition wherein the gain is 1 (0 dB), then oscillations will occur. However, it can be seen from FIGS. 4a, 4b and 4c that the open loop characteristic of the phase of the high frequency gain rising type indicated by the curve ① in FIG. 4a exhibits a maximum phase margin mg compared with those of the high frequency gain flat type shown in FIG. 4b and the high frequency gain dropping type shown in FIG. 4c, and consequently, it is highest in stability. Accordingly, even when the loop characteristic is fluctuated upon mounting or removal of the headphone apparatus 10, howling and so forth can be prevented effectively.

As described above, in the present embodiment, by constructing, a headphone apparatus having a noise canceling function using a headphone of the non-reflective type, the equalizer 3 and the amplifier 4 as those of the high frequency gain rising type as indicated by the lines ① of FIG. 3, increase in stability, expansion of the frequency band in which noise can be canceled and increase in noise attenuation amount can be realized. Further, since the flat frequency band of the closed loop characteristic can be made wider, the distortion frequency characteristic is improved and also the sound quality is improved.

It is to be noted that, while the characteristic of the high frequency rising type of the embodiment is +4 dB/oct, a sufficient effect in practical use can be achieved with the characteristic of +2 dB/oct or more.

The present invention is not limited to the specific embodiment described above, and various modifications are possible without departing much from the spirit and scope of the invention as set forth herein. The acoustic pipe of the headphone of the non-reflective type need not have an acoustic material provided therein, and it is basically required that the acoustic pipe have a cavity therein. Also the position at which the microphone unit is mounted on the acoustic pipe may be on the wall face of the acoustic pipe on the same side as the position at which the loudspeaker unit is mounted.

What is claimed is:

1. A headphone, comprising:

an acoustic pipe having an inner diameter substantially equal to an inner diameter of an external auditory canal of a user of the headphone, said acoustic pipe having a mounting portion provided at one end thereof for being mounted on an outer ear of the user, said acoustic pipe having an acoustically non-reflective end at another end thereof;

a loudspeaker unit provided on one side of said acoustic pipe with a sound emitting face thereof facing an inside of said acoustic pipe;

a microphone unit provided on another side of said acoustic pipe with a sound collecting face thereof facing the inside of said acoustic pipe; and a feedback circuit for feeding back an output signal of said microphone unit to an input side of said loudspeaker unit, said feedback circuit including equalizer means to which the output signal of said microphone unit and a signal to be supplied to said loudspeaker unit are supplied, said equalizer means having an open loop characteristic, wherein an attenuation characteristic of said equalizer means in a frequency band higher than a frequency band in which noise can be canceled has a rising slope.

2. A headphone according to claim 1, wherein said equalizer means has an open loop characteristic wherein the attenuation characteristic of said equalizer means in a frequency band in which the gain is lower than 1, corresponding to a high frequency portion outside of the frequency band in which noise can be canceled, has a rising slope.

3. A headphone according to claim 2, wherein said equalizer means has a gain characteristic which rises by +2 dB/oct or more outside the frequency band in which noise can be canceled.

4. A headphone according to claim 2, wherein said equalizer means includes a subtractor for subtracting the output signal of said microphone unit from the signal to be supplied to said loudspeaker unit, an equalizer to which an output signal of said subtractor is supplied, and an amplifier to which an output signal of said equalizer is supplied, and the characteristic provided by said amplifier and said equalizer is an open loop characteristic wherein the attenuation characteristic of said equalizer means in the frequency band higher than the frequency band in which noise can be canceled in which the gain is lower than 1 has a rising slope.

* * * * *